United States Patent [19]

Lui et al.

[11] Patent Number: 5,620,419
[45] Date of Patent: Apr. 15, 1997

[54] PORT STABILIZER RING

[75] Inventors: Chun K. Lui, Monroeville; Louis Goode, Evans City, both of Pa.

[73] Assignee: Cook Pacemaker Corporation, Leechburg, Pa.

[21] Appl. No.: 324,107

[22] Filed: Oct. 14, 1994

[51] Int. Cl.$^6$ .................................................. A61M 5/32
[52] U.S. Cl. .............................................. 604/116; 604/175
[58] Field of Search ................................. 604/115, 116, 604/891.1, 51, 180, 175

[56] References Cited

U.S. PATENT DOCUMENTS

| | | | |
|---|---|---|---|
| 4,380,234 | 4/1983 | Kamen | 604/180 |
| 4,767,410 | 8/1988 | Moden et al. | 604/175 |
| 4,813,939 | 3/1989 | Marcus | 604/177 |
| 5,100,387 | 3/1992 | Ng | 604/116 |
| 5,171,228 | 12/1992 | McDonald | 604/116 |
| 5,248,301 | 9/1993 | Koenig et al. | 604/164 |
| 5,342,311 | 8/1994 | Dirina | 604/116 |
| 5,350,360 | 9/1994 | Ensminger et al. | 604/175 |

*Primary Examiner*—Todd E. Manahan
*Attorney, Agent, or Firm*—Richard J. Godlewski

[57] ABSTRACT

A noninvasive, perforate, self-centering locator (10) facilitates engagement of a needle or cannula with a vascular access device (44) of the type having a subcutaneously implanted infusion port (46) and an infusion chamber (48) contained in the infusion port (46), the infusion chamber (48) being covered by a septum (52). The locator (10) is exemplified by a port stabilizer ring (12) having a central opening (18) with an interior diameter greater than the diameter of the septum (52) but less than the greatest diameter of the infusion port (46). The stabilizer ring (12) or other embodiment of the locator (10) is pressed on the skin (45) over the site of the infusion port (46), and simultaneously visually locates the septum (52) for the user while stabilizing the infusion port (46) with respect to the skin (45) and underlying tissues, permitting ready penetration of the skin (45) and septum (52) by a needle or cannula (58). The locator (10) most conveniently includes a radial split, such as the split (20) of the stabilizer ring (12), permitting withdrawal without interfering with any needle or cannula (58) engaged with the chamber (48) of the infusion port (46). The stabilizer ring (12) or other embodiment of the locator (10) preferably includes a circular, oval or arc-like planar annulus (14), and a ramp (16) extending inwardly from the planar annulus (14). Methods of using the noninvasive, perforate, self-centering locator (10) to facilitate engagement of a needle or cannula (58) with an implanted vascular access device (44) are also disclosed.

32 Claims, 3 Drawing Sheets

PORT STABILIZER RING

TECHNICAL FIELD

This invention relates generally to surgical procedures, and more particularly to techniques of chemotherapy, infusion, blood sampling, and the like.

BACKGROUND OF THE INVENTION

Chemicals have long been administered to treat or prevent illness. Chemotherapy is optimized by carefully controlling the amount, timing and location in the body of drug dosing. Implanted vascular access devices (VADs) are particularly useful for the prolonged, repeated or targeted injection of medications, sparing a patient the constant search for peripheral veins to achieve venous access. Moreover, VADs obviate the need for a dressing to cover the access site, once the incision from implantation of the device heals.

VADs typically include a catheter and an access or infusion port. The catheter of the VAD is implanted in fluid communication with an artery or vein, while the infusion port is implanted below the skin of the patient. Access to the port, and thereby to the catheter and the artery or vein, is obtained by puncturing the skin with a needle or cannula, until fluid communication with the port is achieved. Typically, the infusion port has an internal infusion chamber in fluid communication with the catheter, sealed or covered by a self-healing top septum, and the needle or cannula pierces the septum to achieve the ultimately desired access to the patient's vascular system.

While conventionally referred to as "infusion" ports, the ports of VADs are also useful for blood sampling and for the supply of blood products and nutrients. Reference to "infusion" ports throughout this application therefore includes ports useful or used for these other purposes, in addition to infusion.

It is important that the infusion port of the VAD is implanted deeply enough to avoid necrosis of the overlying tissue and erosion of the port through the skin, typically, at least about 12 to 13 mm beneath the skin of the patient. While this usually avoids tissue necrosis, it also makes it difficult to visually determine the site of the desired injection site, that is, the site of the infusion port and septum. This is particularly difficult since the sutured incision or scar from the implantation of the VAD is not an adequate guide to the precise location of the port or septum. (Whether the implantation site will have a sutured incision or a scar depends upon the length of time that has passed since implantation of the VAD.) Indeed, it is highly preferred during implantation of a VAD that the port is offset from the incision, precisely to avoid injections through the sutured incision or scar.

Because of the depth of implantation of the port, the conventional method of piercing the skin over the port and septum entails repeated manual palpation of the site. The site is first palpated to generally locate the port, and then palpated a second time (after site sterilization) to precisely locate the port and septum and stabilize their position during introduction of the needle or cannula. This conventional method is subject to some drawbacks, however. It involves repeated contact with the patient's skin, prolonged positioning of the fingers near the site, and prolonged positioning of the fingers nearer the needle or cannula than might be desired. All of these increase the possibility of contamination of the site or cross-contamination of the person performing the injection. Of course, palpation is made even more difficult when a low-profile infusion port is used, but low-profile ports are highly desirable because they require a relatively smaller subcutaneous pocket during implantation.

Numerous devices exist to aid piercing the skin with a needle or cannula and engaging an implanted VAD. One such device is shown in U.S. Pat. No. 4,813,939 (Marcus, Mar. 21, 1989). That patent is directed to an infusion apparatus for use with implantable access ports. The infusion apparatus includes a disc housing and wings hingedly secured to the housing for convenient grasping of the apparatus during use. While useful for its intended purpose, this device and devices like it do not have any provision for visually locating a subcutaneously implanted infusion port, nor for stabilizing the port itself against underlying tissue or against the pressure needed to introduce the needle or cannula.

SUMMARY OF THE INVENTION

The foregoing problems are solved and a technical advance is achieved in an illustrative locator or infusion port stabilizer ring as disclosed herein. Applicant has discovered that these and other problems can be overcome by pressing a noninvasive, perforate, self-centering locator on the skin over the approximate location of the infusion port of an implanted vascular access device prior to engagement of a needle or cannula with the VAD, in order to facilitate such engagement. The needle or cannula can be part of an infusion set, an injection syringe, an aspirating syringe, a blood sample tube, or the like.

More particularly, the present invention is directed to a method or improvement in a method of accessing a VAD implanted at a site beneath the skin of a patient, which comprises pressing a noninvasive, perforate, self-centering locator on the skin at the site to visually locate the site and stabilize the port with respect to the skin and underlying tissue, prior to passing a needle or cannula through the locator and through the skin into fluid communication with the VAD. Preferably, the method is carried out with a VAD having an implanted catheter; an implanted infusion port connected to the catheter; an infusion chamber contained in the port but which is in fluid communication with the catheter; and a self-healing top septum associated with the port, covering or sealing the infusion chamber. "Perforate" means merely that when the locator is placed over the site of the infusion port, the needle or cannula is able to pass through the locator anywhere within the general outline of the locator.

The method is also preferably carried out with a locator which also functions as a stabilizer, to stabilize the infusion port in all directions when the septum is pierced by the needle or cannula. In such a case, the locator preferably comprises a port stabilizer ring having a planar annulus and a ramp extending inwardly of the annulus. The annulus can be circular, oval or arc-shaped, and defines a central opening having an interior diameter greater than the diameter of the septum but less than the diameter of the infusion port, these diameters being measured in the general plane of the skin surface overlying the infusion port. The ring is conveniently split in a radial direction, which allows the ring to be removed from the site once the needle or cannula has engaged the infusion chamber, without interfering with the needle or cannula, or requiring that the needle or cannula be withdrawn. A graspable flange is preferably connected to the annulus and flange opposite the radial split, allowing easy removal of the ring from the site.

The locator or ring is preferably generally rigid, that is, it is sufficiently rigid when pressed upon by a user's fingers to press at least somewhat into the patient's skin, forming a bulge of skin over the infusion port, thereby providing the desired visual indication of the location of the septum. A physiologically inert but sterilizeable material such as a styrene-butadiene copolymer is particularly useful for the locator or ring.

The user of the locator can be a health care practitioner, or can be the patient himself or herself. In either case, the locator or ring can be provided with an adhesive to cause it to remain over the site while the patient manipulates the needle or cannula. Conveniently, the locator or ring can include small holes through it, and the holes covered with adhesive tape.

Again, as mentioned above, the word "infusion" is used in its broadest conventional sense, including all conventional techniques of vascular access which entail repeated or prolonged use of a needle or cannula. Such techniques include the supply of blood products such as whole blood or plasma, the supply of nutrients such as saline solution or solubilized protein, blood sampling (for example, for the continuous or intermittent monitoring of blood constituents), or the like.

The method of the present invention can further comprise the preliminary step of implanting the VAD with its infusion port and infusion chamber.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which.

It should be noted that the views of FIGS. 2 through 4 are drawn proportionately to scale, with some dimensions indicated below, and other dimensions evident from an inspection of the figures.

DETAILED DESCRIPTION

With reference first to FIGS. 1 through 4, a noninvasive, perforate, self-centering locator 10 according to the present invention is thereshown which is capable of performing two functions simultaneously: visually locating the septum of a subcutaneous infusion port, and stabilizing the port during engagement with a needle or cannula. In its first preferred embodiment, the locator 10 is configured as a split ring 12 having a planar annulus 14 and a ramp 16 extending inwardly of the planar annulus 14. The annulus 14 can be circular, oval or arc-shaped, and is shown as circular in this particular embodiment.

The ramp 16 defines a central opening 18 of the ring 12, through which a needle or cannula may be passed, as described below. The ring 12 includes a radial split 20 permitting withdrawal of the ring 12 when the needle or cannula is passed through the central opening 18. The ring 12 also includes a graspable flange 22 opposite the radial split 20, connected to and positioned perpendicularly to the planar annulus 14 and the ramp 16, to facilitate removal of the ring 12 from the injection site, that is, from the skin over the infusion port.

The specific dimensions of the planar annulus 14 and the ramp 16 are selected in light of the dimensions of the particular infusion port implanted in a particular patient. More particularly, they are selected to give the ring 12 an exterior diameter greater than the diameter of the infusion port, measured in the general plane of the overlying skin. They are also selected to give the central opening 18 of the ring 12 an interior diameter greater than the diameter of the septum of the infusion port, but less than the maximum diameter of the port itself. For example, when intended for use with the preferred VAD described below, the planar annulus 14 preferably has an exterior diameter of approximately 2 inches and an inside diameter of approximately 1.75 inches. The ramp 16 preferably has a matching outside diameter of approximately 1.75 inches, and an interior diameter of approximately 1 inch, thereby giving the ring 12 a central opening 18 having a diameter of 1 inch.

Conveniently, the radial split 20 is about 0.219 inches wide, and the flange 22 is about 0.080 inches wide, 0.5 inches long, and 0.250 inches high. Also conveniently, the planar annulus 14 and the ramp 16 are about 0.062 inches thick, and the top of the ramp 16 lies about 0.137 inches above the bottom of the annulus 14. This yields a particularly preferred ramp angle of about 12.3°, although ramps having angles of about 7° to about 17° are also preferred in the present invention. Again, these dimensions should be tailored to the particular VAD employed, taking into account such factors as the typical depth of implantation of the infusion port, the size of the septum, and the location of the implantation site, particularly the nature of the underlying tissues.

The composition of the locator 10, here exemplified by the port stabilizer ring 12, must also be taken into account when its dimensions are optimized. It is preferred that the locator 10 is composed of a physiologically innocuous and sterilizeable material, such as a styrene-butadiene copolymer. A preferred copolymer is K-Resin KR01 from Phillips 66. ("K-Resin KR01" is believed to be a tradename of Phillips 66.) Other materials may of course be used, and the particular dimensions of the locator 10 selected accordingly, so long as the resulting locator 10 is generally rigid. In this regard, "generally rigid" means that the locator 10 is sufficiently rigid to stabilize the infusion port during use, and to provide a bulge of skin or some other visual indication of the location of the septum of the infusion port.

Of course, the ring 12 (or other embodiment of the locator 10) need not include a ramp 16 which is continuously formed, or continuous with the annulus 14. For example, the ramp 16 could instead be formed as a plurality of inwardly projecting arms or members (not shown). They would still define a central opening 18 between them through which the infusion port septum can be located and the infusion port stabilized. Other useful ramp configurations should be evident to anyone even rudimentarily skilled in this area, in view of the instant disclosure.

Figure 10:
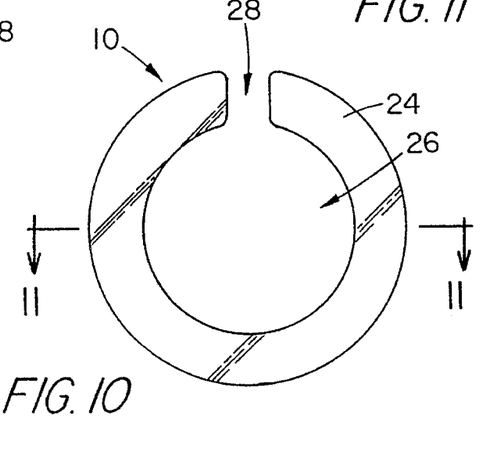
FIG. 10 is a top view of another preferred embodiment of the locator of the present invention.
Figure 11:
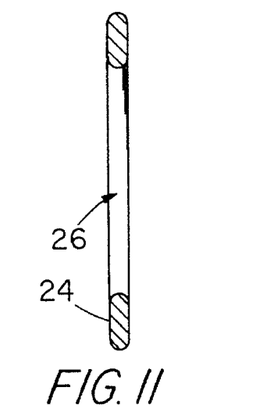
FIG. 11 is a cross-sectional view taken along line 11—11 of FIG. 10.

Indeed, it should be quite apparent that the ramp 16 itself is merely convenient and not necessarily required in all embodiments of the present invention. With reference to FIGS. 10 and 11, a locator 10 configured as a flat disk 24 is thereshown. The flat disk 24 is useful with single port devices, as is the ring 12, and includes a central opening 26 and radial split 28 comparable to the opening 18 and radial split 20 of the ring 12. However, no ramp or other member comparable to the ramp 16 of the ring 12 is provided. The flat disk 24 is still expected to be useful with the same VAD ports as the ring 12, although the particular structure of the ring 12 may make it more rigid or more convenient for use than the flat disk 24.

Figure 8:
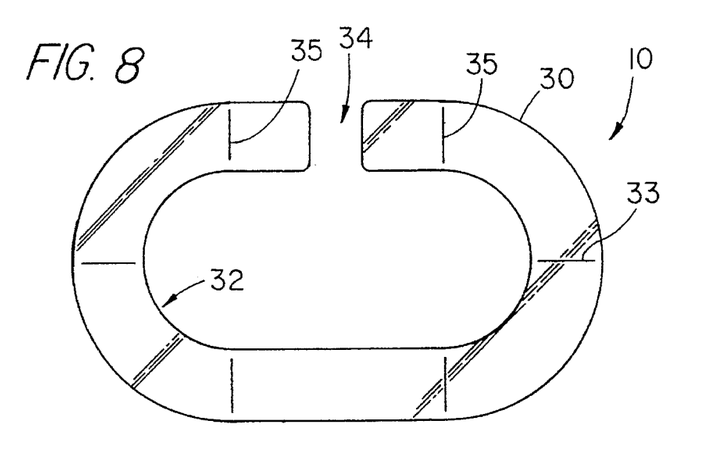
FIG. 8 is a top view of another preferred embodiment of the locator of the present invention.

The locator 10 of the present invention need not be circular in shape, and is expected to be useful with VADs having dual infusion ports or other port shapes. With particular reference to FIG. 8, an embodiment of the locator 10 configured as a flat, oval, dual port locator 30 is thereshown having an oval central opening 32 and a lateral split 34. The lateral split 34 is dimensioned and positioned to allow removal of the dual port locator 30 from a site having two needles or cannulae engaged with the implanted VAD. The dual port locator 30 bears on it two horizontal registering lines 23, and four vertical registering lines 35 disposed perpendicularly to the horizontal lines 33. The intersections of the lines 33 and 35 indicate the centers of the two septa of the dual infusion port. Other plural-port configurations should be readily apparent to those skilled in the art, such as those with a split located 90° from the disclosed position of the lateral split 34, without further disclosure.

Figure 9:
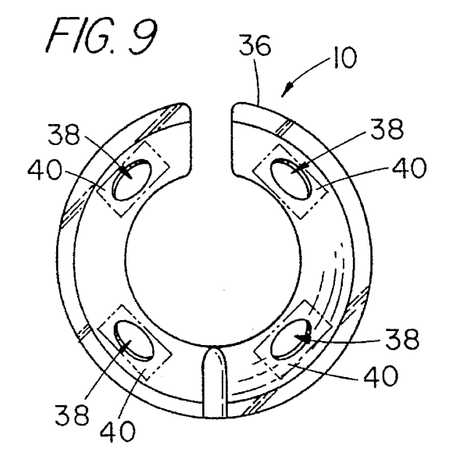
FIG. 9 is a top view of another preferred embodiment of the locator of the present invention.

In the above embodiments, it is probably desirable to maintain pressure on the locator 10 during use in order to achieve the stabilization function. This may not always be possible, for example, if the device is to be used by a patient in the absence of a health care practitioner. The patient will typically need the same hand to position the locator and to manipulate the needle or cannula. Alternatively, the health care practitioner may have to leave the patient for a few minutes during the prep procedure, yet want to avoid repeating the locating procedure. In either case, it would be desirable to provide the locator with an adhesive to permit it to remain in the proper location, for example, while the patient penetrates the skin and septum with the needle or cannula. An embodiment of the locator 10 having an adhesive is shown in FIG. 9, generally configured as a self-adhering stabilizer ring 36 comprising the same elements as the ring 12 of FIGS. 1 through 4, but additionally having a plurality of holes 38 formed through it, spaced from its central opening 42. Pieces of adhesive tape 40 (shown in phantom) are positioned over the holes 38 and are exposed by the holes 38 to the underlying skin. The locator 36 can be pressed with one hand onto the patient's skin, and will remain in place while the same hand manipulates the needle or cannula. While the locator 36 will probably not achieve the same degree of port stabilization as the ring 12, some stabilization can still be provided during penetration of the skin, and the advantage of visually locating the septum is, of course, still enjoyed. A disparate or separate adhesive or adhesive layer (such as double-sided adhesive tape or medical grade adhesive) can be used in place of the holes 38 and tape 40 positioned, for example, on the bottom of the ring 36.

Figure 1:
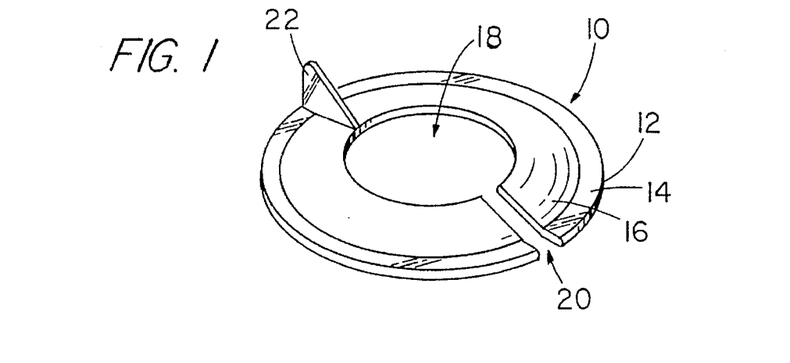
FIG. 1 is a perspective view of a first preferred embodiment of the locator of present invention.
Figure 2:
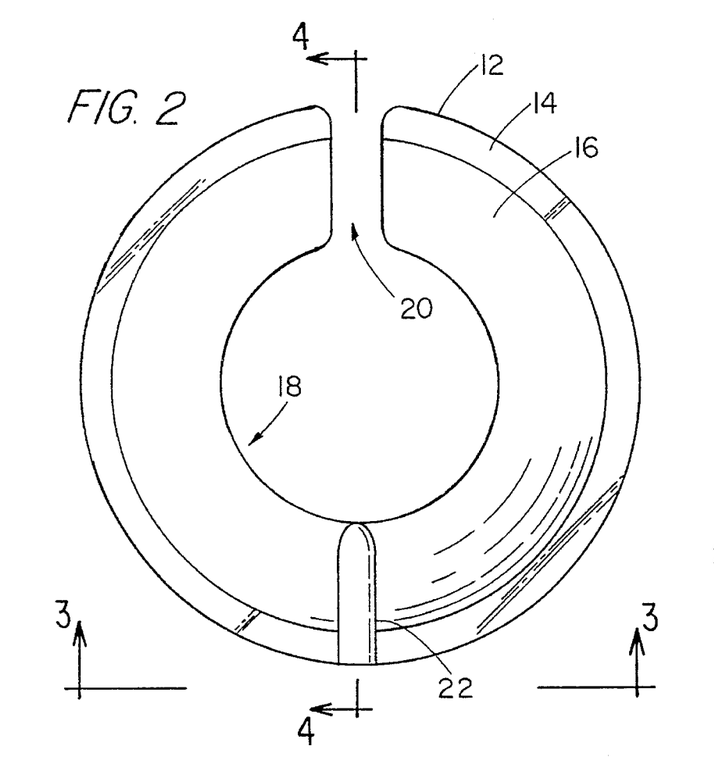
FIG. 2 is a top view of the first preferred embodiment of the present invention.
Figure 3:
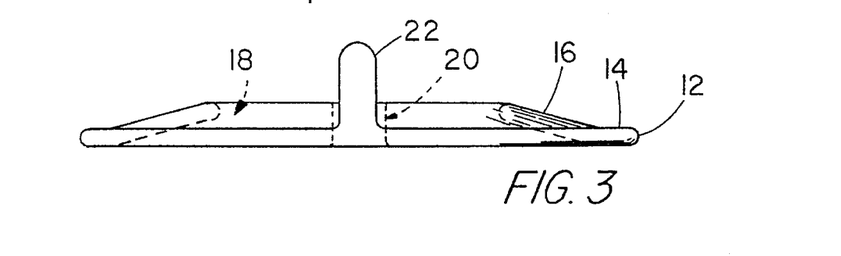
FIG. 3 is an end view taken along line 3—3 of FIG. 2.
Figure 4:
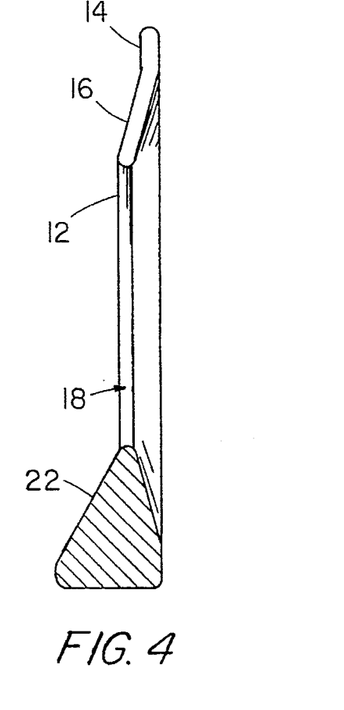
FIG. 4 is a cross-sectional view taken along line 4—4 of FIG. 2.
Figure 5:
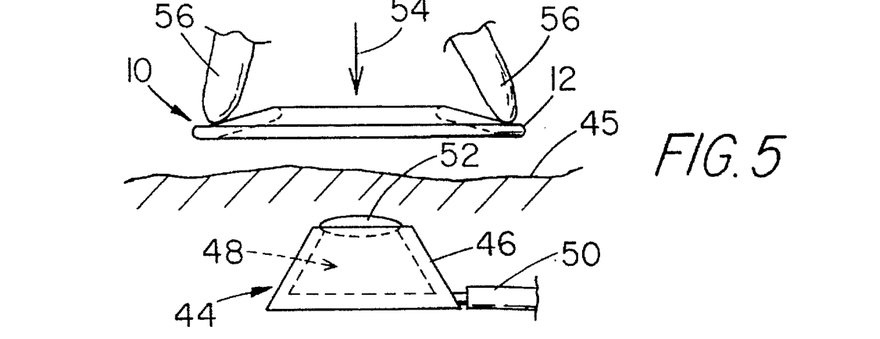
FIGS. 5 through 7 are perspective views of the use of the first preferred embodiment of the present invention.
Figure 6:
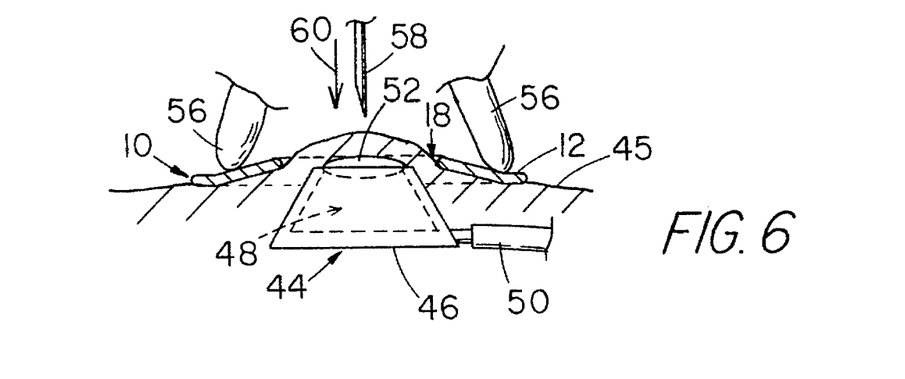
Figure 7:
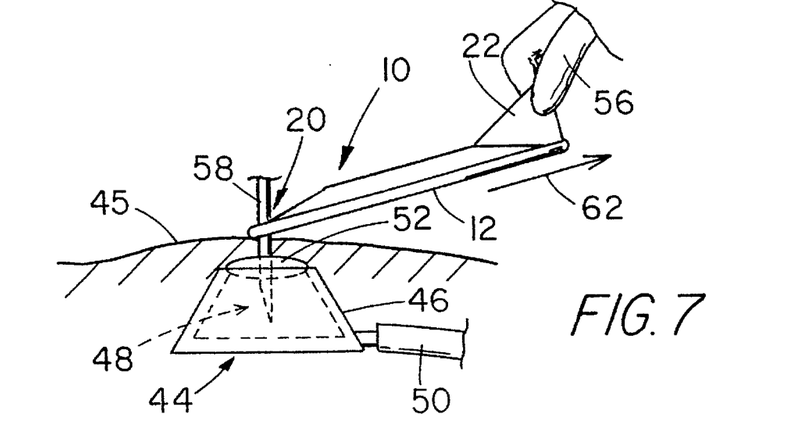

As indicated above, the locator 10 of the present invention is particularly useful with a vascular access device of the type having an implanted catheter, an implanted infusion port, an infusion chamber contained in the infusion port, and a self-healing top septum covering or sealing the infusion chamber. A particularly preferred VAD for use in conjunction with the locator of the present invention is the Vital-Port Vascular Access System. ("Vital-Port" is a registered trademark of Cook Pacemaker Corporation, Leechburg, Pa.) As shown in FIGS. 5 through 7, the particularly preferred VAD 44 as implanted beneath the skin 45 of a patient includes an implanted infusion port 46 having an infusion chamber 48 (in phantom) contained in it, in fluid communication with an implanted catheter 50. The infusion port 46 has a self-healing top septum 52 positioned over and sealing the infusion chamber 48.

The VAD is implanted in the conventional fashion with proper care and attention paid to good surgical practices, aseptic technique and prevention of contamination of the implant site. A general familiarity with the appropriate procedures is presumed; the salient points of the preferred method of implantation are:

1. Preparation of the VAD. All air is flushed from the infusion port, infusion chamber and catheter using heparinized saline (100 IU/ml, unless otherwise noted). If the catheter is not preattached to the infusion port, the filled catheter is closed with a clamp or hemostat on a section that will be removed when the catheter is implanted. If the catheter is preattached to the infusion port, the distal end of the filled catheter is instead kept elevated. All flushing, during both implantation and use of the VAD, should be performed with a syringe of at least 10 ml capacity, to avoid building up unacceptably high pressures in the infusion port, the infusion chamber, and the catheter.

2. Port placement considerations. (a) It is preferred to position the infusion port at a location where it will be supported by an underlying bony structure. It is also preferred to position the port at a location where the septum will be easy to access after implantation. Common sites for the infusion port are the deltoid-pectoral groove, the intra-clavicular space between the third and fourth ribs, the sternum, and the lower portion of the rib cage. The location should also be convenient and comfortable for the patient (at least, as comfortable as possible under the circumstances), for example, on the left side if the patient is right-handed.

(b) As explained further below, implantation of the VAD requires making an incision to allow introduction of the catheter, and to allow formation of a subcutaneous pocket to contain the infusion port. The incision should not be significantly larger than the length of the base (or other long dimension) of the port, while the pocket should be located so that the port septum does not lie directly under the incision line.

3. Catheter placement considerations. The tip of the catheter should be placed in an area of high blood flow, typically lying freely in a blood vessel. Preferred catheter access sites are the subclavian vein, the internal jugular, the external jugular, and the cephalic vein. An exemplary catheter position would exit the infusion port with a gentle curve and, for example, enter the subclavian vein and extend to the junction of the superior vena cava and the right atrium. However, a medial catheter placement should be avoided when introducing the catheter into the subclavian vein in particular, using a percutaneous technique, as catheter shearing with a more medial route has been reported. Placement of the catheter in direct contact with the clavicle should also be avoided.

4. Implantation of the VAD. (a) Once the port site is chosen, an analgesic (for example, a local anesthetic) is administered to the patient, the site for the infusion port scrubbed several times with "Betadine," and the incision made. ("Betadine" is a registered trademark of The Purdue Frederick Company, Norwalk, Conn., for povidone-iodine topical antiseptic microbicide solutions.) The appropriate vein is punctured with, for example, a guide wire, and a pocket for the port is created by blunt dissection, at least about 12 to 13 mm below the surface of the skin. Fat is excised from the pocket as required.

(b) If the catheter is preattached to the infusion port, the appropriate catheter length is measured and cut straight across the distal end of the catheter. The catheter is then advanced from the port site to the selected access vessel. The distal end of the catheter is positioned at the desired location using standard surgical technique.

(c) If the catheter is instead separate from the infusion port, its distal end is positioned at the desired location in the selected access vessel by standard surgical techniques for percutaneous central venous introduction or for cutdown procedure. The catheter is then advanced from the selected access vessel to the port pocket site, using a standard tunneling device if required. The catheter is trimmed to the appropriate length by cutting straight across its proximal end. It is then confirmed that the port is filled with heparinized saline, and the proximal end of the catheter attached to the infusion port.

5. Flow verification. Before the port pocket is closed, it is verified that there is unimpeded fluid flow through the septum, port and catheter. Verification is conveniently carried out by blood aspiration and heparin flushing using a non-coring needle and a 10 ml syringe. It is important to avoid reflux during withdrawal of the needle from the septum.

6. Port sutures and site closure. The port is anchored to the fascia, for example, with three nonabsorbable sutures. The incision is then closed in two layers with absorbable sutures, making sure that the port septum does not lie directly beneath the incision. The port should be accessed before sending the patient to the recovery area.

7. Post-operative care and general accessing procedures. It is recommended that the VAD be flushed with saline and a heparin lock be reestablished at 24 and 48 hours after implantation. Aseptic technique should always be used in accessing the VAD. Only single-use, non-coring needles or cannulae should be used to access the VAD. Needles should always be inserted perpendicularly to the septum, and each needle should be inserted slowly until it contacts the bottom of the infusion chamber. The implanted VAD should never be left open to the air, and any needle or cannula engaged with it should never be rocked or tilted. Before and after drug administration, the VAD should be flushed with saline to remove heparin; between the sequential administration of different drugs, the VAD should be flushed with saline to remove each prior drug. The VAD should be flushed with 5 ml of heparinized saline after each patient treatment, and in any event at least once every four weeks.

Again, a familiarity with the surgical techniques and requirements relating to vascular access devices is presumed. What is important for the purpose of the present application is that the VAD is, in fact, properly implanted.

Use of the noninvasive, perforate, self-centering locator of the present invention to facilitate engagement of a needle or cannula with an implanted VAD can now be easily understood. The overall procedure is as follows: First, the patient is placed in a supine position, or in such other position as is appropriate to the location of the infusion port 46. The port site is inspected for swelling or redness, and the patient asked if any unusual pain has been experienced. Any problems discovered should be addressed by the attending physician before proceeding further.

The infusion port site is then palpated to initially locate the septum 52. Conveniently, the thumb and forefinger of one hand are used to stabilize the base of the port 46 while the forefinger of the other hand palpates the area in a circular motion.

Once the septum 52 is initially located, a sterile field is created in the area, using "Betadine" swab sticks moved in a circular motion, beginning at the center of the port site until an area about 4 inches in diameter is covered. The swabbing is repeated twice, allowing a drying time between each.

Any infusion set to be used is then primed with normal saline solution, about 0.6 ml if a Y-set is used, or about 0.4 ml if a Y-set is not used. Any other needle or cannula to be used should be primed as appropriate.

As shown in FIG. 5, the locator 10, for example, the port stabilizer ring 12, is positioned on the skin 45 over the infusion port 46 and downward pressure is applied (in the direction of the arrow 54) with the fingers 56 until the ring 12 centers itself over the infusion port 46 and the septum 52. This centering simultaneously visually locates the septum 52 and stabilizes the position of the infusion port 46.

While downward pressure on the ring 12 is maintained, as shown in FIG. 6 a non-coring, 19 to 22 gauge needle 58 (or other needle or cannula, for example, an infusion set needle) is centered over the central opening 18 of the ring 12, and the needle 58 moved perpendicularly downward in the direction of the arrow 60 to puncture the skin 45 and pierce the septum 52. It is important to confirm that the tip of the needle 58 is in contact with the bottom of the infusion chamber 48 (FIG. 7) before proceeding with any injection or infusion through the needle 58.

The ring 12 can then be removed from the skin 45 by relaxing the pressure of the fingers 56 on it, grasping the flange 22 with the fingers 56, and sliding the ring 12 away from the site, in the direction of the arrow 62. The needle 58 is allowed to pass through the split 20 in the ring 12, preferably without contacting the ring 12.

Blood sampling, injection or infusion through the needle 58 can then be carried out in any conventional fashion. It is recommended that, with the needle 58 initially in place, a blood return be aspirated in order to ensure proper placement of the needle 58 and the catheter 50. During any infusion or injection, the subcutaneous tissue should be carefully observed for any signs of infiltration into the tissue by the materials or drugs supplied. Catheter tip clogging and vessel thrombosis have been associated with drug extravasation, and extravasation can be minimized or avoided by careful insertion of the needle 58 into the septum 52.

Once blood sampling, injection or infusion through the needle 58 is completed, the port stabilizer ring 12 can be reintroduced to the site just prior to removal of the needle 58. As with penetration, the ring 12 spreads the pressure needed for removal of the needle 58 over a relatively large area, minimizing discomfort to the patient.

It is particularly convenient, however, to obtain any needed blood samples after the aspiration check, but before any injection or infusion. If this is done, care should be taken to immediately saline flush the infusion set or needle, the port chamber and the catheter of blood. At the end of the saline flush, the last milliliter of saline should be clamped closed to prevent reflux. If no further treatment is required, a heparin lock of 5 ml heparinized saline should be instituted. Indeed, the final step of using the VAD should always be to establish a heparin lock.

Other possible procedures merit some comments. When medication is to be administered by Bolus injection, the saline flush syringe is discarded and replaced with a medication syringe. The clamp is opened, and the medication slowly injected.

If continuous infusion is instead contemplated (typically for 24 hours to several days, depending upon the particular disease being treated), administration may require the use of an extension set with a clamp to prevent air embolus and reflux of the medication or blood. An external pump or intravenous drip can be used for continuous infusion. Moreover, as with any prolonged infusion cycle, antibiotic ointment should be applied to the puncture site to avoid any possible local infection.

The patient should of course be instructed to observe the puncture site and report any subcutaneous infiltration, needle dislodgement, swelling or burning. There are two other possible complications to be particularly aware of, first, an inability to obtain blood samples, and second, catheter occlusion. If blood samples cannot be obtained through the needle or cannula, the port and needle should be irrigated with 5 to 10 ml of normal saline solution. The needle should also be repositioned by rotating it clockwise to be sure that the needle bevel is not occluded. If catheter occlusion appears to occur, it may arise from the catheter tip resting against the blood vessel wall; the patient can be repositioned to remedy the occlusion, if this is the source.

It should be clear from the foregoing disclosure that the present invention facilitates engagement of a needle or cannula with an implanted vascular access device. The septum of the VAD is visually located while the infusion port of the device is simultaneously stabilized in all directions during puncture of the skin and penetration of the septum. Patient discomfort during both insertion and withdrawal of the needle or cannula is also minimized, since the applied force necessary to stabilize the port is spread by the locator or stabilizer ring over a relatively large area.

It is to be understood that the above-described port stabilizer ring is merely an illustrative embodiment of the principles of this invention, and that other infusion port locators and methods for using them may be devised by those skilled in the art without departing from the spirit and scope of the invention. It is also to be understood that the invention is directed to embodiments both comprising and consisting of the disclosed elements.

What is claimed is:

1. A noninvasive, infusion port stabilizer for use in conjunction with a vascular access device (44) implanted beneath the skin (45) of a patient, the access device (44) having an infusion port (46), an infusion chamber (48) contained in the infusion port (46), and a top septum (52) over the infusion chamber (48), and the stabilizer comprising a rigid ring (12, 36) having a planar annulus (14) and a ramp (16) extending inwardly of the annulus (14); wherein the ramp (16) defines a central ring opening (18, 42) having an interior diameter greater than the diameter of the septum (52) but less than the maximum diameter of the infusion port (46); wherein the ring (12, 36) is radially split (20), thereby allowing withdrawal of the ring (12, 36) transversely to any needle or cannula (58) which may be in fluid communication with the infusion chamber (48), without interfering with any such needle or cannula (58); and wherein the ring (12, 36) has an exterior diameter greater than the diameter of the infusion port (46); such that when the port stabilizer ring (12, 36) is positioned on the skin (45) of the patient over the general area of the infusion port (46), pressure on the annulus (14) and the ramp (16) centers the port stabilizer ring (12, 36) over the infusion port (46), simultaneously stabilizing the position of the infusion port (46) and visually locating the septum (52) for access.

2. The port stabilizer of claim 1, including an adhesive (40) for affixing the ring (36) to the patient's skin (45).

3. The port stabilizer of claim 2, wherein the ring (36) includes at least one hole (38) exposing a portion of the patient's skin (45), and the adhesive comprises adhesive tape (40) positioned over the at least one hole (38).

4. The port stabilizer of claim 1, wherein the ring (12,36) is composed of a physiologically inert and sterilizeable material.

5. The port stabilizer of claim 4 wherein the material is styrene-butadiene copolymer.

6. The port stabilizer of claim 1, wherein the annulus (14) is generally circular.

7. The port stabilizer of claim 1, wherein the annulus (14) is generally oval.

8. The port stabilizer of claim 1, wherein the ramp (16) slopes at an angle of about 7 to about 17 degrees.

9. The port stabilizer of claim 1, further comprising at least one graspable flange (22) connected to both the annulus (14) and the ramp (16), and extending away from the skin (45) of the patent.

10. A noninvasive, infusion port stabilizer for use in conjunction with a vascular access device (44) implanted beneath the skin (45) of a patient, the access device (44) having an infusion port (46), an infusion chamber (48) contained in the infusion port (46), and a top septum (52) over the infusion chamber (48), and the stabilizer comprising a ring (36) having a planar annulus (14) and a ramp (16) extending inwardly of the annulus (14); wherein the ramp (16) defines a central ring opening (42) having an interior diameter greater than the diameter of the septum (52) but less than the maximum diameter of the infusion port (46), and wherein the ring (36) has an exterior diameter greater than the diameter of the infusion port (46); such that when the port stabilizer ring (36) is positioned on the patient's skin (45) over the general area of the infusion port (46), pressure on the annulus (14) and the ramp (16) centers the port stabilizer ring (36) over the infusion port (46), simultaneously stabilizing the position of the infusion port (46) and visually locating the septum (52) for access; wherein the ring (36) includes at least one hole (38) exposing a portion of the patient's skin (45), and adhesive tape (40) positioned over the at least one hole (38) for affixing the ring (36) to the patient's skin (45); wherein the ring (36) is radially split (20), thereby allowing withdrawal of the ring (36) transversely to any needle or cannula (58) which may be in fluid communication with the infusion chamber (48), without interfering with any such needle or cannula (58); wherein the ring (36) is composed of a rigid styrene-butadiene copolymer; wherein the ring (36) is generally circular; wherein the ramp (16) slopes at an angle of about 7 degrees to about 17 degrees; and wherein the port stabilizer ring (36) further comprises at least one graspable flange (22) opposite the radial split (20), connected to both the annulus (14) and the ramp (16), and extending away from the skin (45) of the patient.

11. In a method of accessing a vascular access device (44) implanted at a site beneath the skin (45) of a patient, the access device (44) having an infusion port (46), an infusion chamber (48) contained in the infusion port (46), and a top septum (52) over the infusion chamber (48), and the method including the step of passing a needle or cannula (58) through the skin (45) and into fluid communication with the device (44), the improvement comprising:

pressing a noninvasive, self-centering perforate locator (10) on the skin (45) at the site to visually locate the site before passing the needle or cannula (58) through the skin (45), wherein the locator (10) comprises a rigid ring (12, 36) having a planar annulus (14) and a ramp (16) extending inwardly of the annulus (14); wherein the ramp (16) defines a central ring opening (18, 42) having an interior diameter greater than the diameter of the septum (52) but less than the maximum diameter of the infusion port (46); wherein the ring (12, 36) is radially split (20), thereby allowing withdrawal of the ring (12, 36) transversely to any needle or cannula (58) which may be in fluid communication with the infusion chamber (48), without interfering with any such needle or cannula (58); and wherein the ring (12, 36) has an exterior diameter greater than the diameter of the infusion port (46); such that when the port stabilizer ring (12, 36) is positioned on the skin (45) of the patient over the general area of the infusion port (46), pressure on the annulus (14) and the ramp (16) centers the port stabilizer ring (12, 36) over the infusion port (46), simultaneously stabilizing the position of the infusion port (46) and visually locating the septum (52) for access; and passing the needle or cannula (58) through the perforate locator (10) and through the skin (45) into fluid communication with the device (44).

12. The method of claim 11 comprising the further step of removing the perforate locator (10) from the skin (45) while the needle or cannula (58) remains in communication with the vascular access device (44).

13. The method of claim 11 wherein the pressing step is carried out using a split ring (12, 36).

14. The method of claim 11 comprising the further step of adhering the locator (10) to the skin (45) before passing the needle or cannula (58) through the skin (45).

15. The method of claim 11 wherein the pressing step is carried out with a locator (10) which is generally circular in shape.

16. The method of claim 11 wherein the pressing step is carried out with a locator (10) having a graspable flange (22) connected to both the annulus (14) and the ramp (16), and extending away from the skin (45) of the patient.

17. The method of claim 11 wherein the locator (10) is pressed against the skin (45) continuously during the step of passing the needle or cannula (58) through the skin (45) and the septum (52), thereby stabilizing the port (46) in all directions during the passing step.

18. A method for accessing a vascular access device (44) implanted at a site beneath the skin (45) of a patient, the access device (44) having an infusion port (46), an infusion chamber (48) contained in the infusion port (46), and a top septum (52) over the infusion chamber (48) and the method comprising:

pressing a self-centering perforate locator (10) on the skin (45) at the site to visually locate the site, wherein the locator (10) comprises a rigid ring (12, 36) having a planar annulus (14) and a ramp (16) extending inwardly of the annulus (14); wherein the ramp (16) defines a central ring opening (18, 42) having an interior diameter greater than the diameter of the septum (52) but loss than the maximum diameter of the infusion port (46); wherein the ring (12, 36) is radially split (20), thereby allowing withdrawal of the ring (12, 36) transversely to any needle or cannula (58) which may be in fluid communication with the infusion chamber (48) without interfering with any such needle or cannula (58); and wherein the ring (12, 36) has an exterior diameter greater than the diameter of the infusion port (46); such that when the port stabilizer ring (12, 36) is positioned on the skin (45) of the patient over the general area of the infusion port (46), pressure on the annulus (14) and the ramp (16) centers the port stabilizer ring (12, 36) over the infusion port (46), simultaneously stabilizing the position of the infusion port (46) and visually locating the septum (52) for access; and passing a needle or cannula (58) through the perforate locator (10) and through the skin (45) into fluid communication with the device (44).

19. The method of claim 18 comprising the further step of removing the perforate locator (10) from the skin (45) while the needle or cannula (58) remains in fluid communication with the vascular access device 44).

20. The method of claim 18 wherein the pressing step is carried out using a split ring (12, 36).

21. The method of claim 18 comprising the further step of adhering the locator (10) to the skin (45) before passing the needle or cannula (58) through the skin (45).

22. The method of claim 18 wherein the pressing step is carried out with a locator (10) which is generally circular in shape.

23. The method of claim 18 wherein the pressing step is carried out with a locator (10) having a graspable flange (22) connected to both the annulus (14) and the ramp (16), and extending away from the skin (45) of the patient.

24. The method of claim 18 wherein the locator (10) is pressed against the skin (45) continuously during the step of passing the needle or cannula (58) through the skin (45) and the septum (52), thereby stabilizing the port (46) in all directions during the passing step.

25. A surgical method comprising the steps of:

implanting a vascular access device (44) at a site beneath the skin (45) of a patient, the access device (44) having an infusion port (46), an infusion chamber (48) contained in the infusion port (46), and a top septum (52) over the infusion chamber (48);

pressing a self-centering perforate locator (10) on the skin (45) at the site to visually locate the site, wherein the locator (10) comprises a rigid ring (12, 36) having a planar annulus (14) and a ramp (16) extending inwardly of the annulus (14); wherein the ramp (16) defines a central ring opening (18, 42) having an interior diameter greater than the diameter of the septum (52) but less than the maximum diameter of the infusion port (46); wherein the ring (12, 36) is radially split (20), thereby allowing withdrawal of the ring (12, 36) transversely to any needle or cannula (58) which may be in fluid communication with the infusion chamber (48), without interfering with any such needle or cannula (58); and wherein the ring (12, 36) has an exterior diameter greater than the diameter of the infusion port (46); such that when the port stabilizer ring (12, 36) is positioned on the skin (45) of the patient over the general area of the infusion port (46), pressure on the annulus (14) and the ramp (16) centers the port stabilizer ring (12, 36) over the infusion port (46), simultaneously stabilizing the position of the infusion port 46) and visually locating the septum (52) for access; and passing a needle or cannula (58) through the perforate locator (10) and through the skin (45) into fluid communication with the device (44).

26. The method of claim 25 comprising the further step of removing the perforate locator (10) from the skin (45) while the needle or cannula (58) remains in fluid communication with the vascular access device (44).

27. The method of claim 25 wherein the pressing step is carried out using a split ring (12, 36).

28. The method of claim 25 comprising the further step of adhering the locator (10) to the skin (45) before passing the needle or cannula (58) through the skin (45).

29. The method of claim 25 wherein the pressing step is carried out with a locator (10) which is generally circular in shape.

30. The method of claim 25 wherein the pressing step is carried out with a locator (10) having a graspable flange (22) connected to both the annulus (14) and the ramp (16), and extending away from the skin (45) of the patient.

31. The method of claim 25 wherein the locator (10) is pressed against the skin (45) continuously during the step of passing the needle or cannula (58) through the skin (45) and the septum (52), thereby stabilizing the port (46) in all directions during the passing step.

32. A method for accessing a vascular access device (44) implanted at a site beneath the skin (45) of a patient, the vascular access device (44) having an infusion port (46), an infusion chamber (48) contained in the infusion port (46), and a top septum (52) over the infusion chamber (48), and the method comprising:

pressing a self-centering perforate locator (10) on the patient's skin (45) at the site, the locator (10) comprising a ring (36) having a planar annulus (14) and a ramp (16) extending inwardly of the annulus (14); wherein the ramp (16) defines a central ring opening (42) having an interior diameter greater than the diameter of the septum (52) but less than the maximum diameter of the infusion port (46), and wherein the ring (36) has an exterior diameter greater than the diameter of the infusion port (46); wherein the ring (36) includes at least one hole (38) exposing a portion of the patient's skin (45) and adhesive tape (40) positioned over the at least one hole (38) for affixing the ring (36) to the patient's skin (45); wherein the ring (36) is radially split (20), thereby allowing withdrawal of the ring (36) from the site transversely to any needle or cannula (58) which may be in fluid communication with the infusion chamber (48), without interfering with any such needle or cannula (58); wherein the ring (36) is composed of a rigid styrene-butadiene copolymer; wherein the ring (36) is generally circular; wherein the ramp (16) slopes at an angle of about 7 degrees to about 17 degrees; and wherein the perforate locator (10) further comprises at least one graspable flange (22) opposite the radial split (20), connected to both the annulus (14) and the ramp (16), and extending away from the skin (45) of the patient; such that when the locator (10) is positioned on the patient's skin (45) over the general area of the infusion port (46), pressure on the annulus (14) and the ramp (16) centers the perforate locator (10) over the infusion port (46), simultaneously stabilizing the position of the infusion port (46) and visually locating the septum (52) for access; and passing a needle or cannula (58) through the central opening (18) of the perforate locator (10), the skin (45) and the septum (52) into fluid communication with the infusion chamber (48) of the vascular access device (44).

* * * * *